(12) United States Patent
Sandner

(10) Patent No.: US 9,766,188 B2
(45) Date of Patent: Sep. 19, 2017

(54) METHOD AND DEVICE FOR OPTICALLY INSPECTING FAULTS

(71) Applicant: VIPROTRON GMBH, Darmstadt (DE)

(72) Inventor: Andreas Sandner, Weiterstadt (DE)

(73) Assignee: VIPROTRON GMBH, Darmstadt (DE)

( * ) Notice: Subject to any disclaimer, the term of this patent is extended or adjusted under 35 U.S.C. 154(b) by 63 days.

(21) Appl. No.: 14/894,437

(22) PCT Filed: Jun. 3, 2014

(86) PCT No.: PCT/EP2014/061456
§ 371 (c)(1),
(2) Date: Nov. 27, 2015

(87) PCT Pub. No.: WO2014/195296
PCT Pub. Date: Dec. 11, 2014

(65) Prior Publication Data
US 2016/0103081 A1    Apr. 14, 2016

(30) Foreign Application Priority Data
Jun. 3, 2013    (DE) .................. 10 2013 105 693

(51) Int. Cl.
*G01B 11/24*     (2006.01)
*G01N 21/958*    (2006.01)
*G01N 21/88*     (2006.01)

(52) U.S. Cl.
CPC ....... *G01N 21/958* (2013.01); *G01B 11/2433* (2013.01); *G01N 21/8806* (2013.01); *G01N 2201/061* (2013.01)

(58) Field of Classification Search
CPC ............. G01N 21/958; G01N 21/8806; G01N 2201/061; G01B 11/2433
See application file for complete search history.

(56) References Cited

U.S. PATENT DOCUMENTS 4,459,027 A * 7/1984 Kafri ................. G02B 27/60
                                                250/237 G
5,128,550 A   7/1992 Erbeck
(Continued)

FOREIGN PATENT DOCUMENTS

DE        10203595 A1    8/2003
GB        2 065 299 A    6/1981
WO        2008083497 A1  7/2008

OTHER PUBLICATIONS

International Search Report dated Oct. 9, 2014 for corresponding International App. PCT/EP2014/061456.

*Primary Examiner* — Michael P Stafira
(74) *Attorney, Agent, or Firm* — WRB-IP LLP

(57) ABSTRACT

In a method for optically checking a large-area three-dimensional object an illumination surface of parallel light beams is generated using a light source, a large-area three-dimensional object is partly or completely illuminated by the illumination surface, and a change of the parallel light beams of the illumination surface through the object is detected, wherein a projection surface is arranged on an object face opposite the light source, and the object shadow cast on the projection surface by the illumination surface is detected using an optical detection device. The strip-shaped light curtain is produced with a Fresnel lens. The shadow is detected using an optical lens system or a CCD camera. The dimensions of the object parallel to the projection surface are ascertained and compared with specified reference values. The projection surface is an opaque panel made of a translucent material or a surface-treated glass pane.

23 Claims, 2 Drawing Sheets

(56) References Cited

U.S. PATENT DOCUMENTS

2002/0154814 A1 10/2002 Gerhard et al.
2007/0008522 A1 1/2007 Hill et al.
2010/0134789 A1 6/2010 Boutinon et al.

* cited by examiner

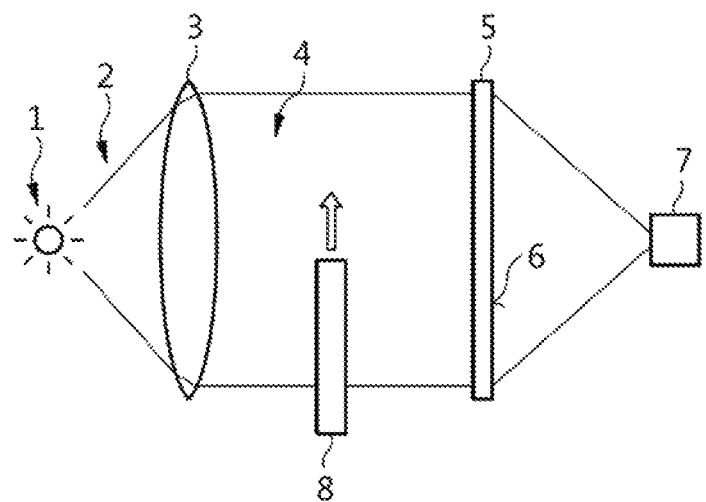
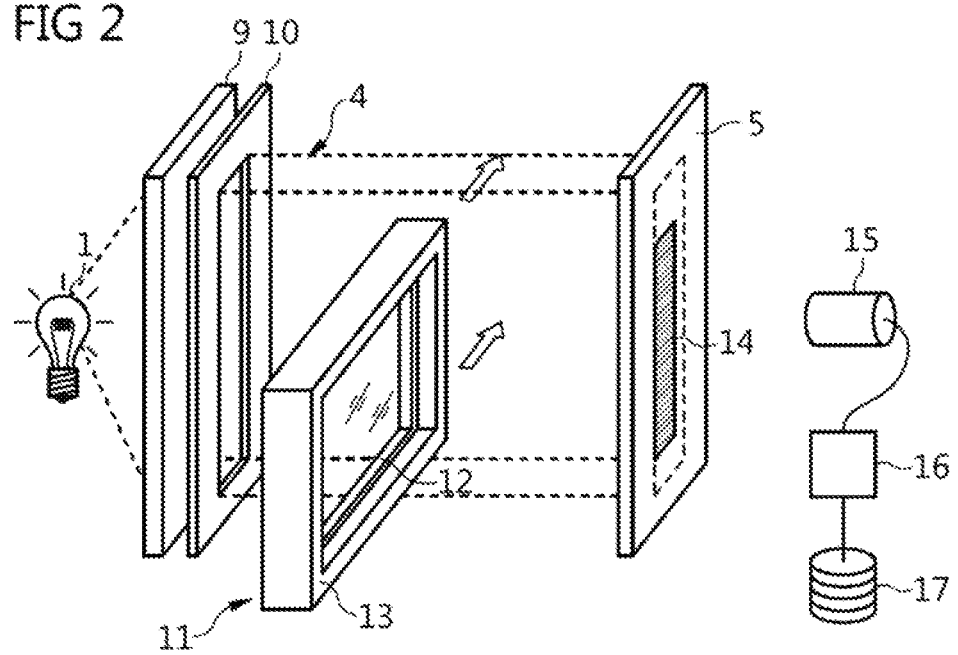

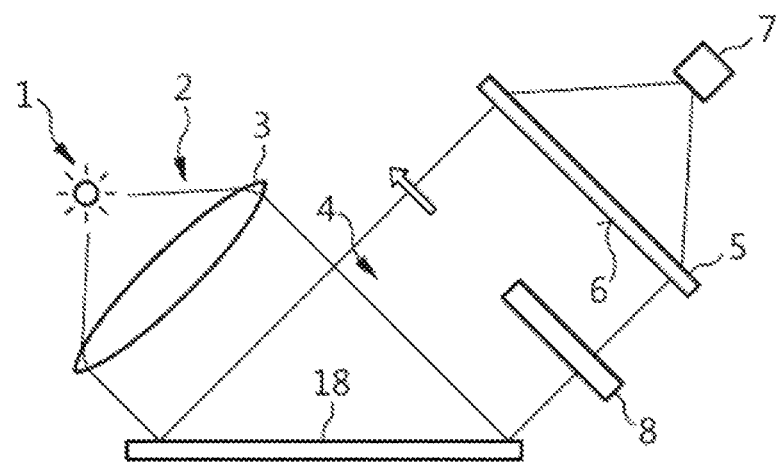
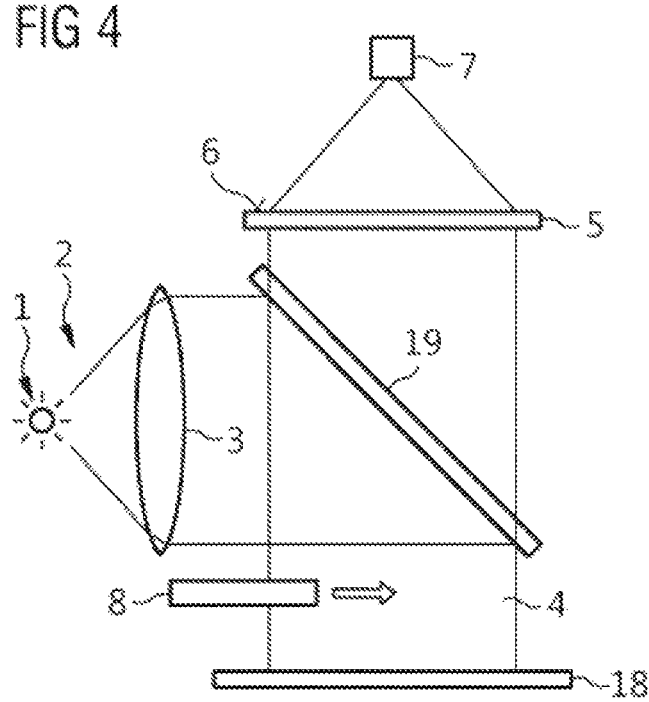

METHOD AND DEVICE FOR OPTICALLY INSPECTING FAULTS

BACKGROUND AND SUMMARY

The invention concerns a method for optical fault inspection, or checking of an object, wherein an illumination surface is created from parallel light beams with a light source, wherein the object is at least partly illuminated by the illumination surface and wherein a change in the parallel light beams of the illumination surface by the object is detected.

Such methods are used for example by a manufacturer for optical checking of glass panes. Another area of use of such test methods involves the inspection of framed glass panes and especially multiple glazed and framed window panes during and after their manufacture. Besides defects within the surface of the pane, these test methods serve to check the correct positioning of the glass panes relative to the frame elements. With such test methods one can determine whether a frame element was fixed in the intended position relative to the glass pane, or whether there is an unwanted skewing of the frame element going beyond the usual tolerance range of a few millimeters and making the window element unusable.

It is known from the prior art how to use optical detection devices with telecentric lenses having very large depth of focus. With telecentric lenses, edges of three-dimensional objects can be detected relatively sharply and dimensions determined precisely. However, the size of the object is limited to the diameter of the telecentric lens or a front lens arranged therein. After a diameter of several centimeters, telecentric lenses are hardly still economically advisable for the determination of dimensions of three-dimensional objects, on account of the high manufacturing costs.

The dimensions of glass panes or window elements often amount to more than 0.5 in or 1 m and can be 2 m, 3 m, or more, especially in one direction.

In a method described for example in EP 2 108 116 A1, a glass pane is transfixed by a collimated light curtain which is generated by a light source. The parallel light beams, which have been influenced by the glass pane, are focused again on an imaging surface by a lens system on a side lying opposite the light source and recorded by a camera. The maximum simultaneously recordable surface, or the maximum dimension of the light curtain, is limited essentially by the size and quality of the lens system with which the light curtain of parallel light can be focused again on the imaging surface or in the camera after passing through the object. For large panes of glass, the design expense is very high.

A method of this kind is known from EP 1 866 625 A2, in which the parallel light beams after passing through a transparent flat object are detected and evaluated with strip-shaped scanning device on a side of the object situated opposite the light source. Suitable scanning devices are commercially available and are used for example in fax transmittal machines or in digital copier systems. A lens system is not required for focusing the parallel light beams having passed through the object. In order to inspect a large-area object, however, generally several strip-shaped scanner devices need to be combined and evaluated, so that an exact positioning of the several scanner devices relative to each other and to the object is required.

It is therefore desirable to further develop a method of the kind mentioned above so that a quick and reliable detection of large objects is possible with simple design means.

According to an aspect of the present invention, the light beams arriving from the illumination surface are projected onto a projection surface disposed behind the object and the shadow of the object cast on the projection surface by the illumination surface is detected with an optical detection device.

The casting of a shadow is any impairment or possibly slight impairment of the beam path of the light beams coming from the illumination surface and influenced by the object. Consequently, the shadowing includes a complete darkening by light-impenetrable regions of the object as well as a barely visible or undetectable influencing of the light beams by a totally transparent glass pane, for example.

The shadowing can be produced by light with wavelengths within the visible light spectrum. However, it is likewise conceivable and in certain application situations advantageous to generate the shadow by light with wavelengths outside of the visible wavelength region and to use a light source, for example, which emits predominantly or exclusively infrared light or ultraviolet light. The projection surface used to form the shadow and the optical detection device must be adapted or suitable to the wavelength region designed for the shadowing.

The shadowing of the object on the projection surface enables a cheap and reliable detecting and checking of the dimensions of a large-area three-dimensional object. Furthermore, transparent regions of the object can be distinguished from nontransparent regions. Defects within a glass pane which cast a shadow can be quickly detected. A sideways offset of frame elements of a window element leads to a correspondingly displaced or disproportionately broad shadow and can be reliably determined.

With the aid of the projection surface, large-area three-dimensional objects in particular can be checked much more cheaply than with the methods known in the prior art, which require for example the use of telecentric lenses. Objects with dimensions of several centimeters can already be considered to be large-area three-dimensional objects. With suitable components, the projection surface can also be used to cheaply and reliably inspect large-area objects such as glass panes or window elements with side lengths of more than one or two meters, for example.

In order to determine the dimensions of the object in one direction, it is sufficient to inspect the shadow cast by the object in only this direction. According, to one especially advantageous embodiment of the notion of the invention, the object is completely scanned. In this way, the orientation of the object relative to the optical detection device can be checked, for example, so that it is not required to use suitable transport or bearing mechanisms to specify the orientation to the object being inspected. Operator errors or tolerances in the positioning of the object can also be determined and corrected.

In order to make possible the broadest area of an intensely lit illumination surface, the illumination surface is generated with several light sources disposed at a spacing from each other. The plurality of light sources can be disposed in a row or a matrix. It is also possible to arrange different kinds of light sources alongside each other and to combine them arbitrarily with each other as needed.

Preferably, a strip-shaped light curtain is created as the illumination surface and the object and the strip-shaped light curtain are moved relatively to each other. For the detecting and evaluation of the shadow cast on the projection surface, a striplike scanning of the large-area three-dimensional object and thus an essentially one-dimensional detecting and evaluation of the shadowing is especially advantageous. A striplike scanning is considered to be the successive detecting of the shadow strip of the object created with a striplike light source or illumination surface, the illumination surface being, moved relative to the large-area object in order to illuminate all regions of the object in succession. The linear detecting and evaluation of the shadowing can be accomplished cheaply with conventional optical components and evaluated quickly. The light emitted by the one light source or plurality of light sources can be focused in the strip-shaped light curtain in order to accomplish a high contrast of the shadow cast on the projection surface.

If the object is moved and not the light source or the optical detection device, the measurement system can be optimally arranged and adjusted to enable the most precise possible optical measurements.

A strip-shaped light curtain can be created according to one embodiment of the notion of the invention with an optionally multiple-piece Fresnel lens. A Fresnel lens enables relative large-area dimensions with a relatively slight thickness of the Fresnel lens. As compared to a lens of glass or plastic. Fresnel lenses enable a large-area focusing of the light emitted by the light source into a beam of parallel rays, even though the Fresnel lens only has slight thickness and therefore a low weight. A multiple-piece Fresnel lens can be made up of several Fresnel lenses or individual Fresnel lens segments disposed alongside each other.

Preferably, the object is moved past the lighting surface and the projection surface. The light source, the Fresnel lens, the projection surface and an optical detection device can be disposed stationary and be oriented and adjusted relative to each other, so that a large number of objects can then move through the apparatus so set up and be evaluated in a short time. The precision of the measurements can be improved in this way. The inspection process can be performed during the manufacture of the large-area three-dimensional objects or immediately thereafter at a time and place where the large-area three-dimensional objects are being moved and transported, for example, inside a manufacturing assembly line or from a production facility to a storage location.

An economical detection of the shadow cast can be done with an optical lens system. Even large-area projection surfaces can be reliably detected and subjected to an evaluation in this way. The optical lens system can be, for example, a conventional camera lens or a video camera with a digital storage medium, or also without a digital storage medium.

A simple and sufficient inspection system, which at the same time is informative for many applications, involves a determination of dimensions of the object parallel to the projection surface. The dimensions so determined can be compared against given reference values. The size of the shadow cast on the projection surface can be quickly and reliably determined with almost any optical detection device. In many cases, a first decision can already be made by means of the dimensions of the object as to whether the object has passed the inspection or whether to defect has been found, or whether the object needs to undergo a closer and possibly manual inspection.

Especially with transparent objects, such as panes of glass, it is likewise possible to carry out an automated check for defects. For this purpose, one determines irregularities within the object. To the extent that the irregularities, such as flaws, inclusions, bubbles, scratches or streaks cause a discernible change in the shadow, these irregularities can be determined and indicated, or subjected to a further evaluation. It is likewise possible to distinguish the identified irregularities according to predetermined criteria and indicate corresponding information or institute actions depending on the criterion.

The invention also concerns a device for optical inspection of a large-area three-dimensional object. The devices known from the prior art have a light source, a device for producing a lighting surface of parallel light beams and an optical detection device for the detection of a change in the parallel light beams of the lighting surface due to the object.

According to the invention, a projection surface is disposed at a distance from the illumination surface and the optical detection device is suitable to detecting the shadow of an object located in the path of the parallel light beams that is cast by the illumination surface on the projection surface. With the aid of the projection surface, the shadow cast by the object can be made visible. Many commercially available optical detection devices are able to detect the shadow cast on a projection surface. Consequently, it is not necessary to focus the parallel light beams once more on a small-format imaging surface or to use large-format optical detection devices.

The shadow cast by the object on the projection surface can be detected for example with a video camera with a digital storage medium. The optical sensor used can be for example a CCD sensor or a CMOS sensor. For a reliable detection of the shadowing, commercially available cameras or comparable optical lens systems with a continually operating image recording are suitable. Of course, an optical detection device can also have several cameras or several CCD sensors or CMOS sensors.

Depending on the imaging properties of the optical lens system used, a large-area projection surface with a linear dimension of more than one meter and with a sufficient resolution and sufficient contrast can be detected in order to enable the determination and checking of dimensions of the object.

It is possible, and especially advantageous for the detection of large projection surfaces, for the optical detection device to consist of several components, or imaging type image detection devices, whose information can than be combined and further processed in largely automated fashion.

Thanks to the use of a digital optical detection device such as a CCD camera or a CMOS camera, a further processing and evaluation of the raw measured data becomes especially easy.

A large-area lighting surface of parallel light beams can be achieved with the use of an optionally multiple-piece Fresnel lens. In particular for a strip-shaped lighting surface, a long and approximately linear lighting surface can be achieved with a relatively low weight and with slight overall thickness of the Fresnel lens.

It is likewise possible to use another equally suitable optical focusing device in place of a Fresnel lens. For example, a lighting surface of parallel light beams could also be generated by a system of several lens disposed alongside each other. Depending on the light source used, mirror systems can also be used to create an illumination surface with parallel light beams.

According to one advantageous embodiment of the notion of the invention, the projection surface is an opaque pane of a translucent material. The shadowing of the object can be detected in this way on a side of the projection surface facing away from the object, so that the object moving, past the projection surface does not hinder the optical detection of the shadow image on the projection surface. At the same time, this makes it possible to dispose the light source, the device for creating a lighting surface of parallel light beams, the projection surface and the optical detection device along one optical axis, which allows especially advantageous geometrical boundary conditions for a large-area scanning and checking of a three-dimensional object.

A suitable projection surface can be, for example, a surface-treated glass pane, which can both be made economically and also has suitable properties for the imaging and detection of the shadow produced by the object.

It is likewise possible for the projection surface to have an opaque foil or an opaque sheeting. Suitable foils are commercially available as filter foils, for example. An opaque foil can be deposited on an economical transparent backing, such as polymethyl methacrylate, or stretched in a flame.

BRIEF DESCRIPTION OF THE DRAWINGS

A sample embodiment of the notion of the invention shall be explained more closely below, being shown as an example in the drawing. There is shown:

FIG. 1, a schematic representation of the method of the invention for the optical inspection of a large-area three-dimensional object, FIG. 2, a sample representation of a device suitable for implementing the method, FIG. 3, a schematic representation of a modified device suitable for implementing the method, and FIG. 4, a schematic representation of another modified device.

DETAILED DESCRIPTION

In a method for the optical inspection of a large-area three-dimensional object shown schematically in FIG. 1, a beam 2 of noncoherent light, is generated with a light source 1. Using a suitable optical component 3, an illumination surface 4 of parallel light beams is created, which is directed onto a projection surface 5. The projection surface 5 consists of a translucent pane with a matte surface 6. An optical detection device 7 is disposed on one side of the projection surface 5 located opposite the light source 1, with which an image of the projection surface 5 can be recorded.

The projection surface 5 is illuminated with parallel light beams from the illumination surface 4. An object 8 situated between the illumination surface 4 and the projection surface 5 casts a shadow on the projection surface 5. The shadow so cast can be detected and evaluated with the optical detection device 7.

When the object 8 moves through between the illumination surface 4 and the projection surface 5 across the parallel light beams, the shadow cast by the object 8 on the projection surface 5 changes accordingly. Thanks to a continual recording of the shadow with the optical detection device 7, even large-area objects 8 whose dimensions are larger than the dimensions of the illumination surface 4 and the projection surface 5 can be inspected with the above described layout.

By means of the size and shape of the shadow, which is imaged and detected with the optical detection device 7, and by comparing with predetermined reference values, one can determine whether the dimensions of the object 8 fall within predetermined tolerance ranges or whether the object 8 has deviations from the predetermined reference values which can mean that the object 8 does not pass the inspection or needs to undergo a further more comprehensive and possibly manual inspection.

In the sample embodiment shown in FIG. 2, the light generated by the light source 1 is transformed by a Fresnel lens 9 into a strip-shaped illumination surface 4 of parallel light beams. The dimensions of the strip-shaped illumination surface 4 are dictated by a strip-shaped diaphragm 10.

A window element 11 with a glass pane 12 and a frame 13 enclosing the glass pane 12 which is moved between the lighting surface 4 and the projection surface 5 produces a shadow 14 on the projection surface 5. The dimensions of the shadow 14 correspond to the dimensions of the frame 13 of the window element 11, which is moved through between the lighting surface 4 and the projection surface 5. The shadow 14 cast on the projection surface is detected with a CCD camera 15. The raw data recorded by the CCD camera 15 is taken to an evaluation device 16, by means of which the dimensions of the shadow 14 are determined and compared to predetermined reference values, which are fetched from a storage device 17.

In the variant embodiment of a device according to the invention shown schematically and as an example in FIG. 3, the light beam 2 produced with the light source 1 is taken through a lens 3 and impinges sideways on a mirror 18. The parallel light rays impinging on the mirror 18 are reflected in the direction of the projection surface 5, arranged at a distance from the mirror 18. The object 8 can be moved parallel to the projection surface 5 between the mirror 18 and the projection surface 5. The shadow cast by the object 8 on the projection surface 5 is detected with the optical detection device 7.

In the sample embodiment shown schematically in FIG. 4 of another modified device, the light beam 2 produced by the light source 1 is made parallel by the lens 3 and projected onto a semitransparent mirror 19. A portion of the light beam 2 is reflected in the direction of the mirror 18. Thanks to the path of the parallel beam 2 from the semitransparent mirror 19 to the totally reflecting mirror 18 and back, the object 8 can be moved as parallel as possible to the reflecting mirror 18. The shadow cast in this way by the object 8 on the projection surface 5 disposed behind the semitransparent mirror 19 can be detected by means of the optical detection device 7.

The variant embodiments of the device of the invention described as examples in FIGS. 3 and 4 are especially suitable when space relations are tight. The path of the parallel beam 2 described in FIG. 4 has a double passage through the object 8, so that a shadowing caused for example by faults in glass surfaces is amplified and imaged with greater contrast in the shadow cast on the projection surface 5.

The invention claimed is:

1. A method for optical fault inspection of an object, wherein an illumination surface is created from parallel light beams with a light source, wherein the object is at least partly illuminated by the illumination surface and wherein a change in the parallel light beams of the illumination surface by the object is detected, wherein the light beams arriving from the illumination surface are projected onto a projection surface disposed behind the object and the shadow of the object cast on the projection surface by the illumination surface is detected with an optical detection device, wherein a strip-shaped light curtain is created as the illumination surface and the object and the strip-shaped light curtain are moved relatively to each other.

2. The method according to claim 1, wherein the object is a large-area three-dimensional object with a shadowing surface larger than 0.25 m$^3$.

3. A method according to claim 1, wherein the object is entirely illuminated.

4. A method according to claim 1, wherein the illumination surface is generated from parallel light beams with several light sources disposed at a spacing from each other.

5. A method according to claim 1, wherein the strip-shaped light curtain is created with an optionally multiple-piece Fresnel lens.

6. A method according to claim 1, wherein the object is moved past the illumination surface and the projection surface.

7. A method according to claim 1, wherein the illumination surface and the projection surface and also optionally the detection device are moved past the object.

8. A method according to claim 1, wherein the detection of the shadow cast can be done with an optical lens system.

9. A method according to claim 1, wherein a determination of dimensions of the object parallel to the projection surface is done.

10. A method according to claim 9, wherein the dimensions of the object so determined are compared against given reference values.

11. A method according to claim 1, wherein irregularities within the object are determined.

12. A device for optical inspection of an object, with a light source, with a device for producing an illumination surface of parallel light beams, and with an optical detection device for the detection of a change in the light beams coming from the illumination surface due to the object, wherein a projection surface is disposed at a distance from the illumination surface and the optical detection device is suitable to detecting the shadow of an object located in the path of the parallel light beams that is cast by the illumination surface on the projection surface, wherein the projection surface is an opaque pane of a translucent material.

13. The device according to claim 12, wherein the object is a large-area three-dimensional object with a shadowing surface larger than 0.25 m$^2$.

14. The device according to claim 12, wherein the device for producing a lighting surface has an optionally multiple-piece Fresnel lens.

15. The device according to claim 12, wherein the device for producing a lighting surface is a system of several lenses disposed alongside each other or a system of several mirrors.

16. The device according to claim 12, wherein the optical detection device has an optical lens system.

17. The device according to claim 16, wherein the optical detection device has at least one camera with a digital storage medium, or without a digital storage medium.

18. The device according to claim 16, wherein the optical detection device has at least one CCD sensor or a CMOS sensor.

19. The device according to claim 12, wherein the optical detection device consists of several components, or imaging type image detection devices.

20. The device according to claim 12, wherein the projection surface is a surface-treated glass pane.

21. The device according to claim 12, wherein the projection surface has an opaque foil or an opaque sheeting.

22. The device according to claim 12, wherein the device has an evaluation device for determining of dimensions of the object and irregularities within the object, connected to the optical detection device.

23. The device according to claim 22, wherein the evaluation device transmits data and is connected to a storage device in which reference values are memorized.

* * * * *